(12) United States Patent
Flohr et al.

(10) Patent No.: US 6,713,499 B2
(45) Date of Patent: Mar. 30, 2004

(54) 7-AMINO-BENZOTHIAZOLE DERIVATIVES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 75 days.

(21) Appl. No.: 10/307,702

(22) Filed: Dec. 2, 2002

(65) Prior Publication Data

US 2003/0153566 A1 Aug. 14, 2003

(30) Foreign Application Priority Data

Dec. 12, 2001 (EP) .............................. 01129272

(51) Int. Cl.[7] ..................... A61K 31/428; C07D 277/82
(52) U.S. Cl. ........................ 514/367; 548/163
(58) Field of Search ........................ 548/163; 514/367

(56) References Cited

U.S. PATENT DOCUMENTS 6,521,754 B2 * 2/2003 Alanine et al. .............. 544/129

FOREIGN PATENT DOCUMENTS

| WO | WO 00 18767 | 4/2000 |
|----|-------------|--------|
| WO | WO 01 97786 | 12/2001 |

* cited by examiner

*Primary Examiner*—Laura L. Stockton
(74) *Attorney, Agent, or Firm*—George W. Johnston; Patricia S. Rocha-Tramaloni; Lyman H. Smith

(57) ABSTRACT

The present invention relates to compounds of the formula

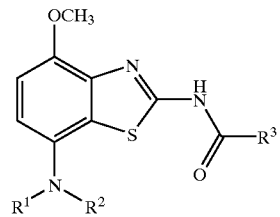

I wherein $R^1$, $R^2$ and $R^3$ are as described herewithin. The compounds of formula I have been found to be adenosine receptor ligands. Specifically, the compounds of the present invention have a good affinity to the $A_{2A}$-receptor and they are therefore useful in the treatment of diseases, related to this receptor.

17 Claims, No Drawings

7-AMINO-BENZOTHIAZOLE DERIVATIVES

BACKGROUND OF THE INVENTION

The present invention generally relates to 7-amino-benzothizaole derivatives that are adenosine receptor ligands. Specifically, the compounds of the present invention have a good affinity to the $A_{2A}$-receptor and a high selectivity to the $A_1$- and $A_3$ receptors.

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptores for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to GC proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtyps is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioural state and (patho) physiological conditions. Under conditions of increased demand and decreased availability of energy (such as hypoxia, hypoglycemia, and/or excessive neuronal activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the Al receptor, adenosine A1 agonists may protect against the injury caused by myocardial ischemia and reperfusion. The modulating influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treament of diabetes mellitus and obesity.

Numerous documents describe the current knowledge on adenosine receptors, for example the following publications:
Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H1113–1116, (1999) or
Naunyn Schmied, Arch. Pharmacol. 362, 375–381, (2000).

SUMMARY OF THE INVENTION

The present invention relates to compounds of the formula I

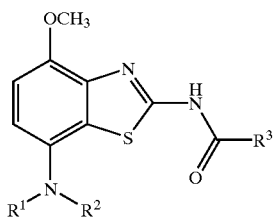

I wherein $R^1$, $R^2$ and $R^3$ are as defined herewithin.

The present invention relates to compounds of formula I per se, the use of compounds of formula I and their pharmaceutically acceptable salts for the manufacture of medicaments for the treatment of diseases related to the adenosine $A_2$ receptor. The present invention further relates to the manufacture of compounds of formula I, medicaments based on compounds of formula I as well as the use of compounds of formula I in the control or prevention of illnesses based on the modulation of the adenosine system. These illnesses include Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The present invention relates to compounds of the formula I

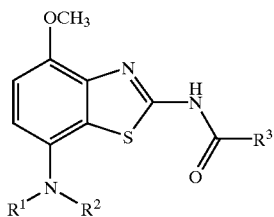

I wherein
$R^1$, $R^2$ are independently selected from the group consisting of hydrogen, lower alkyl, $C_{3-6}$-cycloalkyl, tetrahydropyran-2,3 or 4-yl, piperidin-4-yl, piperidin-4-yl substituted by lower alkyl, —(CH$_2$)$_n$—O-lower alkyl, —(CH$_2$)$_n$—NR'R", —C(O)-lower alkyl, —(CH$_2$)$_n$—C(O)-lower alkyl, —(CH$_2$)$_n$—C(O)—C$_{3-6}$-cycloalkyl, —(CH$_2$)$_n$—C(O)—NR'R", —(CH$_2$)$_n$-phenyl, —(CH$_2$)$_n$-phenyl substituted by lower alkyl, lower alkoxy or NR'R", —(CH$_2$)$_n$-pyridinyl, —(CH$_2$)$_n$-pyridinyl substituted by lower alkyl, lower alkoxy or NR'R", —(CH$_2$)$_n$-morpholinyl, —(CH$_2$)$_n$-tetrahydropyran-2,3 or 4-yl, —(CH$_2$)$_n$-piperidin-1 or 4-yl, —(CH$_2$)$_n$-piperidin-1 or 4-yl substituted by lower alkyl, —C(O)—C$_{5,6}$-cycloalkyl, —C(O)-tetrahydropyran-2,3 or 4-yl, —C(O)-morpholinyl, —C(O)-piperidin-1-yl or —C(O)-pyrrolidin-1-yl, or
$R^1$ and $R^2$ form together with the N atom to which they are attached the ring 2-oxa-5-aza-bicyclo[2.2.1]hept-5-yl, an azetidinyl ring, or an azetidinyl ring substituted by lower alkyl or lower alkoxy;
$R^3$ is lower alkoxy, phenyl, phenyl substituted by halogen, —(CH$_2$)$_n$-halogen, or —(CH$_2$)$_n$—N(R')—(CH$_2$)$_{n+1}$—O-lower alkyl, pyridinyl, pyridinyl substituted by lower alkyl, halogen or morpholinyl, morpholinyl, piperidin-1-yl disubstituted in the 4 position by lower alkyl and —(CH$_2$)$_n$—OH or 2-aza-bicyclo[2.2.2]octane;
n is 1 or 2;
R' and R" are each independently selected from hydrogen or lower alkyl, or together may form with the N atom an azetidinyl-, pyrrolidinyl- or piperidinyl group;
and to pharmaceutically acceptable acid addition salts thereof.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present application are compounds of formula I, wherein one of $R^1/R^2$ is lower alkyl and the other is —(CH$_2$)$_n$—O-lower alkyl and $R^3$ is phenyl, optionally substituted by halogen or —(CH$_2$)$_n$-halogen, for example the following compounds:
N-{4-methoxy-7-[(2-methoxy-ethyl)-methyl-amino]-benzothiazol-2-yl}-benzamide,
4-fluoro-N-{4-methoxy-7-[(2-methoxy-ethyl)-methyl-amino]-benzothiazol-2-yl}-benzamide or
4-chloromethyl-N-{4-methoxy-7-[(2-methoxy-ethyl)-methyl-amino]-benzothiazol-2-yl}-benzamide.

Further preferred are compounds, wherein one of $R^1/R^2$ is lower alkyl and the other is —(CH$_2$)$_n$—O-lower alkyl or $R^1$ and $R^2$ are together with the N atom the group 2-oxa-5-aza-bicyclo[2.2.1]hept-5-yl and $R^3$ is pyridinyl, substituted by morpholine, for example the following compounds:
N-{4-methoxy-7-[(2-methoxy-ethyl)-methyl-amino]-benzothiazol-2-yl}-2-morpholin-4-yl-isonicotinamide or
N-[4-methoxy-7-{(1S,4S)-(2-oxa-5-aza-bicyclo[2.2.1]hept-5-yl)}-benzothiazol-2-yl]-2-methyl-isonicotinamide.

A further preferred group of compounds are those, wherein one of $R^1/R^2$ is —C(O)-lower alkyl and the other is lower alkyl, —(CH$_2$)$_n$—O-lower alkyl or benzyl, optionally substituted by lower alkyl and $R^3$ is phenyl or pyridinyl, which rings are optionally substituted by halogen or lower alkyl, for example the following compounds:

N-{7-[acetyl-(4-methyl-benzyl)-amino]-4-methoxy-benzothiazol-2-yl}-benzamide,
N-[7-(acetyl-methyl-amino)-4-methoxy-benzothiazol-2-yl]-4-fluoro-benzamide,
N-[7-(acetyl-ethyl-amino)-4-methoxy-benzothiazol-2-yl]-4-fluoro-benzamide,
N-[7-(acetyl-benzyl-amino)-4-methoxy-benzothiazol-2-yl]-4-fluoro-benzamide,
N-[7-(acetyl-benzyl-amino)-4-methoxy-benzothiazol-2-yl]-2-bromo-isonicotinamide or
N-{7-[acetyl-(2-methoxy-ethyl)-amino]-4-methoxy-benzothiazol-2-yl}-4-fluoro-benzamide.

Further preferred are compounds, wherein one of $R_1/R^2$ is lower alkyl and the other is lower alkyl or benzyl, optionally substituted by lower alkoxy and $R^3$ is phenyl or pyridinyl, which rings are optionally substituted by morpholinyl, halogen or lower alkyl, for example the following compounds:

N-(7-dimethylamino-4-methoxy-benzothiazol-2-yl)-4-fluoro-benzamide,
N-[7-(benzyl-methyl-amino)-4-methoxy-benzothiazol-2-yl]-4-fluoro-benzamide,
N-[7-(benzyl-methyl-amino)-4-methoxy-benzothiazol-2-yl]-2-methyl-isonicotinamide,
4-fluoro-N-{4-methoxy-7-[(4-methoxy-benzyl)-methyl-amino]-benzothiazol-2-yl}-benzamide,
N-{4-methoxy-7-[(4-methoxy-benzyl)-methyl-amino]-benzothiazol-2-yl}-2-methyl-isonicotinamide,
N-[7-(benzyl-methyl-amino)-4-methoxy-benzothiazol-2-yl]-2-bromo-isonicotinamide or
N-[7-(benzyl-methyl-amino)-4-methoxy-benzothiazol-2-yl]-2-morpholin-4-yl-isonicotinamide.

Further preferred are compounds, wherein one of $R^1/R^2$ is lower alkyl and the other is —$CH_2$—C(O)—N($CH_3$)$_2$ or tetrahydropyran and $R^3$ is phenyl or pyridinyl, which rings are optionally substituted by morpholinyl, halogen or lower alkyl, for example the following compounds:

N-[7-(dimethylcarbamoylmethyl-methyl-amino)-4-methoxy-benzothiazol-2-yl]-4-fluoro-benzamide,
N-[7-(dimethylcarbamoylmethyl-ethyl-amino)-4-methoxy-benzothiazol-2-yl]-4-fluoro-benzamide,
4-fluoro-N-{4-methoxy-7-[methyl-(tetrahydro-pyran-4-yl)-amino]-benzothiazol-2-yl}-benzamide or
N-{4-methoxy-7-[methyl-(tetrahydro-pyran-4-yl)-amino]-benzothiazol-2-yl}-2-morpholin-4-yl-isonicotinamide.

The present compounds of formula I and their pharmaceutically acceptable salts can be prepared by methods known in the art, for example, by processes described below, which process comprises a) reacting a compound of formula

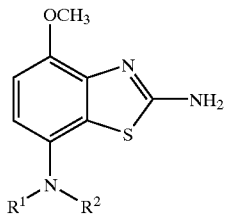
(7)

with a compound of formula

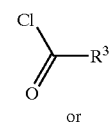
(8)

or

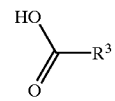
(9)

to yield a compound of formula

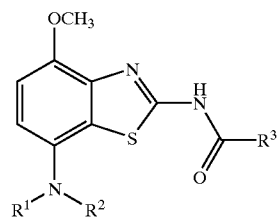
I wherein $R^1$, $R^2$ and $R^3$ are as defined above, and if desired, converting the compounds obtained into pharmaceutically acceptable acid addition salts.

The compounds of formula I may be prepared in accordance with process variant a) and with the following schemes 1 to 4.

Preparation of Compounds of Formula 1

One method of preparation of compounds of formula I is from compounds of formula (7), the preparation of which is shown in reaction scheme 1 below.

Scheme 1

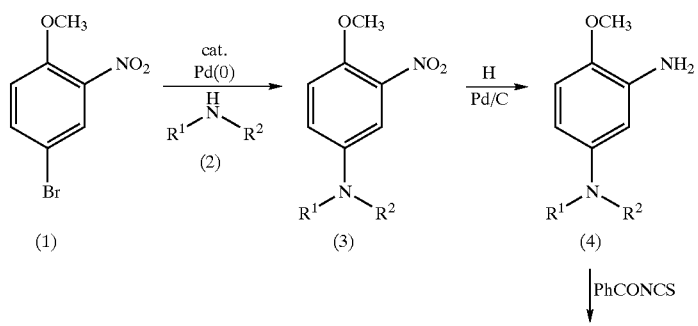

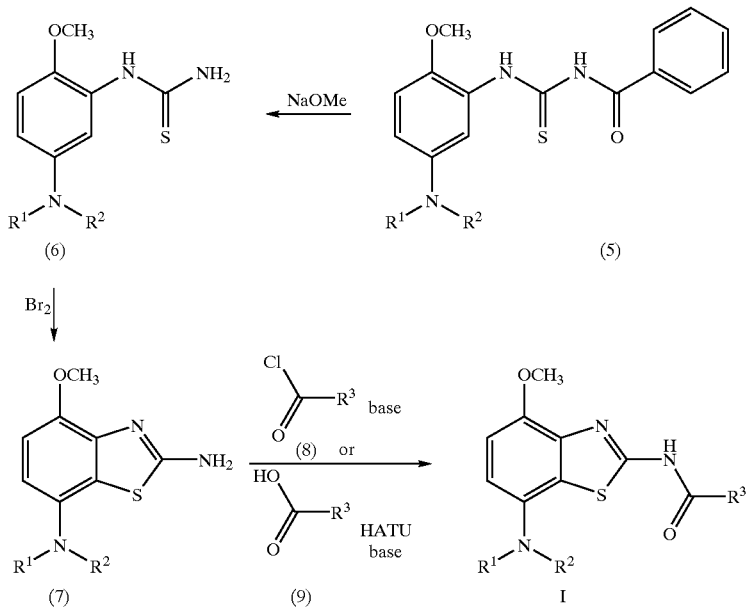

where R$^1$, R$^2$ and R$^3$ are as defined above.

HATU is O-(7-azabenzotriazol-1-yl)-N,N,N',N'M-tetramethyluronium hexafluorophosphate.

Preparation of Compounds of Formula (3)

The starting bromoarene compounds of formula (1) may be obtained commercially, for example from Aldrich, or may be prepared according to methods well known in the art. Similarly, the amine compounds of formula (2) may be obtained commercially, for example from Fluka, or may be prepared according to methods well known in the art.

The bromoarene compound of formula (1) is reacted with an excess of an amine compound of formula (2), or the corresponding amine hydrochloride salt or hydrobromide salt, in an organic solvent, preferably dioxane, containing a palladium catalyst, preferably palladium (II) acetate, and a catalytic amount of a phosphine ligand, preferably 2-(dicyclohexylphosphino)-biphenyl, according to the procedure of Buchwald et al. (*J. Am. Chem. Soc.* 1998, 120, 9722). The reaction is carried out in the presence of a base, such as cesium carbonate, potassium phosphate, triethylamine, or a combination of these. The reaction is carried out at elevated temperature, preferably about 80–100° C., for about 2–24 hours, preferably about 16 hours. The product of formula (3) is isolated by conventional means, and preferably purified by means of chromatography or recrystallization.

Preparation of Compounds of Formula (4)

Compounds of formula (4) may be prepared by hydrogenation of compounds of formula (3) in the presence of a hydrogenation catalyst, preferably 10% palladium on charcoal. These reactions may be carried out in a variety of organic solvents, such as methanol, ethanol, dichloromethane or tetrahydrofuran, preferably a mixture of methanol and dichloromethane, at room temperature and at a pressure of one atmosphere or above, preferably at one atmosphere, for 2–24 hours, preferably about 16 hours. The product of formula (4) is isolated by conventional means, and preferably purified by means of chromatography or recrystallization.

Preparation of Compounds of Formula (5)

One method of preparation of compounds of formula (5) involves treatment of a compound of formula (4) with a slight excess of benzoyl isothiocyanate in acetone at a temperature between room temperature and reflux, preferably at room temperature, for 30–60 minutes, preferably 30 minutes. The product of formula (5) is isolated by conventional means, and preferably purified by means of chromatography or recrystallization.

Preparation of Compounds of Formula (6)

A compound of formula (5) is treated with a substoichiometric amount of an alkali metal alcoholate in the corresponding alcohol solvent, preferably sodium methylate in methanol. The reaction is carried out at room temperature for about 0.5–2 hours, preferably about 1 hour. The product of formula (6) is isolated by conventional means, and preferably purified by means of chromatography or recrystallization.

Preparation of Compounds of Formula (7)

One method of preparation of compounds of formula (7) is by treatment of a compound of formula (6) with a stoichiometric equivalent of bromine in a halogenated organic solvent, preferably chloroform. The reaction is carried out at elevated temperature, preferably at the reflux temperature of the solvent, for about 12–18 hours, preferably about 16 hours. The product of formula (7) is isolated by conventional means, and preferably purified by means of chromatography or recrystallization.

Preparation of Compounds of Formula I

One method of preparation of compounds of formula I is by treatment of a compound of formula (7) with a slight excess of an appropriate acyl chloride of formula (8), which may be commercially available or may be prepared by methods well known in the art. The reaction is carried out in a non-protic organic solvent, preferably a mixture of dichloromethane and tetrahydrofuran, containing a base, preferably N-ethyldiisopropylamine or triethylamine, at room temperature for 2–24 hours, preferably 24 hours. The product of formula I is isolated by conventional means, and preferably purified by means of chromatography or recrystallization.

Alternative Preparation of Compounds of Formula I

An alternative method of preparation of compounds of formula I involves treatment of an appropriate carboxylic acid of formula (9) with a stoichiometric equivalent of a peptide-coupling reagent, preferably O-(7-azabenzotriazol-1-yl)-N,N,N',N'-tetramethyluronium hexafluorophosphate (HATU), in an ethereal solvent, preferably tetrahydrofuran, containing a base, preferably N-ethyldiisopropylamine, at room temperature for 30–90 minutes, preferably 1 hour. This mixture is then treated with a compound of formula (7) in a solvent mixture, preferably a mixture of tetrahydrofuran, dioxane and N,N-dimethylformamide, at room temperature for 16–24 hours, preferably 16 hours. The product of formula I is isolated by conventional means, and preferably purified by means of chromatography or recrystallization.

Alternative Preparation of Compounds of Formula (3)

An alternative method of preparation of compounds of formula (3) is from intermediates of formula (14), the preparation of which is shown in reaction scheme 2 below.

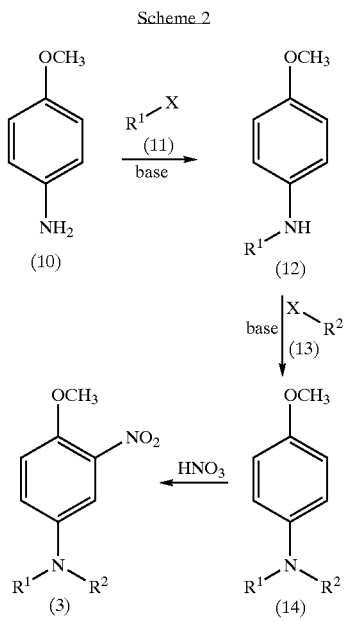

where $R^1$ and $R^2$ are as defined above, and X is Br or I.

Preparation of Compounds of Formula (12)

The starting aryl amines of formula (10) may be obtained commercially, for example from Fluka, or may be prepared according to methods well known in the art. Similarly, the starting alkyl iodide or alkyl bromide compounds of formula (11) may be obtained commercially, for example from Fluka, or may be prepared according to methods well known in the art.

The aryl amine compound of formula (10) is reacted with a stoichiometric equivalent of an alkyl iodide or alkyl bromide compound of formula (II) in an organic solvent, preferably N,N-dimethylformamide or acetonitrile, containing a base, preferably potassium carbonate or N,N-diisopropylethylamine. The reaction is carried out at a temperature between room temperature and the reflux temperature of the solvent, for about 1–48 hours, preferably about 16 hours. The product of formula (12) is isolated by conventional means, and preferably purified by means of chromatography or recrystallization.

Preparation of Compounds of Formula (14)

The starting alkyl iodide or alkyl bromide compounds of formula (13) maybe obtained commercially, for example from Fluka, or may be prepared according to methods well known in the art.

The aryl amine compound of formula (12) is reacted with a stoichiometric equivalent of an alkyl iodide or alkyl bromide compound of formula (13) in an organic solvent, preferably N,N-dimethylformamide or acetonitrile, containing a base, preferably potassium carbonate or N,N-diisopropylethylamine. The reaction is carried out at a temperature between room temperature and the reflux temperature of the solvent, for about 1–48 hours, preferably about 16 hours. The product of formula (14) is isolated by conventional means, and preferably purified by means of chromatography or recrystallization.

Preparation of Compounds of Formula (3)

The compound of formula (14) is reacted with a nitrating agent, such as 65% nitric acid or potassium nitrate in 98% sulfuric acid, in an acidic solvent, such as acetic acid or 98% sulfuric acid. The reaction is carried out at a temperature between 20° C. and 80° C., for about 2–16 hours. The product of formula (3) is isolated by conventional means, and preferably purified by means of chromatography or recrystallization.

Alternative Preparation of Compounds of Formula (7)

An alternative method of preparation of compounds of formula (7) is from intermediates of formula (20), the preparation of which is shown in reaction scheme 3 below.

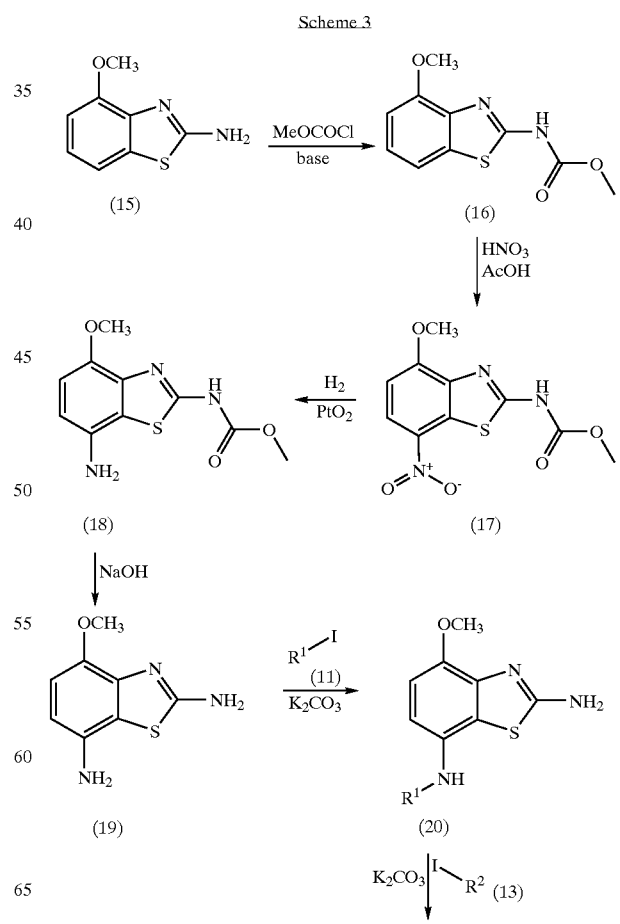

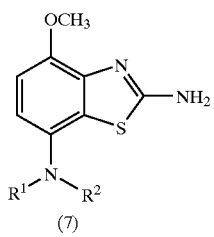

(7)

wherein R$^1$ and R$^2$ are as defined above.

Preparation of Compounds of Formula (16)

The starting 2-amino-benzothiazole compounds of formula (15) maybe obtained commercially, for example from Aldrich, or may be prepared according to methods well known in the art.

The 2-amino-benzothiazole compound of formula (15) is reacted with a stoichiometric equivalent of methyl chloroformate in an organic solvent, preferably dichloromethane, containing a base, preferably pyridine. The reaction is carried out at a temperature between 0° C. and room temperature, preferably at 0° C., for about 1–2 hours, preferably about 1 hour. The product of formula (16) is isolated by conventional means, and preferably purified by means of chromatography or recrystallization.

Preparation of Compounds of Formula (17)

The compound of formula (16) is reacted with a nitrating agent, preferably 65% nitric acid, in an acidic solvent, preferably acetic acid. The reaction is carried out at an elevated temperature, preferably about 70° C., for about 2–16 hours, preferably 4 hours. The product of formula (17) is isolated by conventional means, and preferably purified by means of chromatography or recrystallization.

Preparation of Compounds of Formula (18)

Compounds of formula (18) may be prepared by hydrogenation of compounds of formula (17) in the presence of a hydrogenation catalyst, preferably platinum (IV) oxide. These reactions may be carried out in a variety of organic solvents, such as methanol, ethanol, dichloromethane or tetrahydrofuran, preferably a mixture of methanol and dichloromethane, at room temperature and at a pressure of one atmosphere or above, preferably at one atmosphere, for 2–24 hours, preferably about 16 hours. The product of formula (18) is isolated by conventional means, and preferably purified by means of chromatography or recrystallization.

Preparation of Compounds of Formula (19)

One method of preparation of compounds of formula (19) is by treatment of a compound of formula (18) with an excess of sodium hydroxide or potassium hydroxide in an aqueous solvent, preferably aqueous ethylene glycol. The reaction is carried out at elevated temperature, preferably about 100° C., for about 1–16 hours, preferably about 6 hours. The product of formula (19) is isolated by conventional means, and preferably purified by means of chromatography or recrystallization.

Preparation of Compounds of Formula (20)

The starting alkyl iodides of formula (11) may be obtained commercially, for example from Fluka, or maybe prepared according to methods well known in the art. The compound of formula (19) is reacted with a stoichiometric equivalent of an alkyl iodide compound of formula (11) in an organic solvent, preferably N,N-dimethylformamide, containing a base, preferably potassium carbonate. The reaction is carried out at a temperature between room temperature and the reflux temperature of the solvent, for about 1–48 hours, preferably about 16 hours. The product of formula (20) is isolated by conventional means, and preferably purified by means of chromatography or recrystallization.

Preparation of Compounds of Formula (7)

The starting alkyl iodides of formula (13) maybe obtained commercially, for example from Fluka, or may be prepared according to methods well known in the art. The compound of formula (20) is reacted with a stoichiometric equivalent of an alkyl iodide compound of formula (13) in an organic solvent, preferably N,N-dimethylformamide, containing a base, preferably potassium carbonate. The reaction is carried out at a temperature between room temperature and the reflux temperature of the solvent, for about 1–48 hours, preferably about 16 hours. The product of formula (7) is isolated by conventional means, and preferably purified by means of chromatography or recrystallization.

Alternative Preparation of Compounds of Formula (7) where R$^2$ is —C(O)-lower alkyl, —C(O)—C$_{5,6}$-cycloalkyl, or —C(O)-tetrahydropyran-2,3 or 4-yl.

An alternative method of preparation of compounds of formula (7) from intermediates of formula (20) in the case where R$^2$ contains an acyl group, i.e where R$^2$ is —C(O)-lower alkyl, —C(O)—C$_{5,6}$-cycloalkyl, or —C(O)-tetrahydropyran-2,3 or 4-yl, is shown in reaction scheme 4 below.

Scheme 4

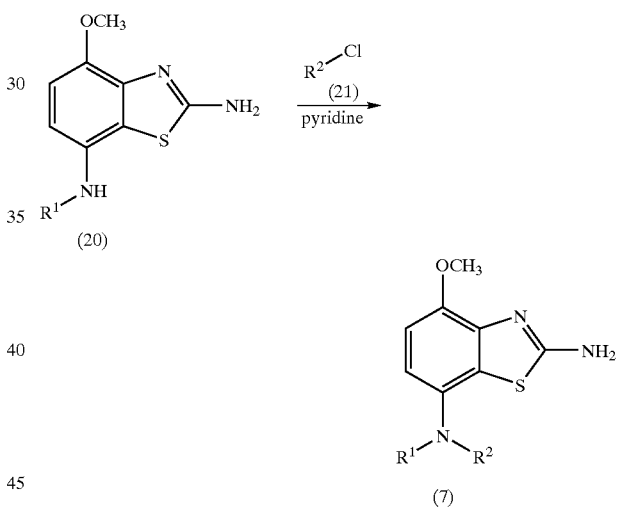

wherein R$_1$ is as defined above and R$^2$ is —C(O)-lower alkyl, —C(O)—C$_{5,6}$-cycloalkyl, —C(O)-tetrahydropyran-2,3 or 4-yl.

The starting acyl chlorides of formula (21) may be obtained commercially, for example from Fluka, or maybe prepared according to methods well known in the art.

The compound of formula (20) is reacted with a stoichiometric equivalent of an acyl chloride compound of formula (21) in an organic solvent, preferably a mixture of dichloromethane and tetrahydrofuran, containing a base, preferably pyridine. The reaction is carried out at a temperature between 0° C. and room temperature, preferably at 0° C., for about 1–16 hours, preferably about 3 hours. The product of formula (7) is isolated by conventional means, and preferably purified by means of chromatography or recrystallization.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 1) 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [3H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. IC50 values were calculated using a non-linear curve fitting program and Ki values calculated using, the Cheng-Prussoff equation.

The preferred compounds show a pKi>7.2.

| Example No. | hA2 (pKi) |
|---|---|
| 1 | 7.28 |
| 2 | 7.42 |
| 3 | 7.43 |
| 6 | 7.28 |
| 10 | 7.94 |
| 12 | 7.13 |
| 14 | 7.41 |
| 15 | 7.21 |
| 16 | 7.81 |
| 17 | 7.22 |
| 19 | 7.88 |
| 20 | 7.21 |
| 21 | 8.00 |
| 24 | 7.97 |
| 25 | 7.28 |
| 26 | 7.75 |
| 28 | 7.31 |
| 30 | 7.58 |
| 32 | 7.48 |
| 35 | 7.96 |
| 37 | 7.25 |
| 38 | 7.33 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing, a compound of formula I or a pharmaceutically acceptable salt thereof and a therapeutically inert carrier are also an object of the present invention, as is a process for their production, which comprises bringing, one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

N-{4-Methoxy-7-[(2-methoxy-ethyl)-methyl-amino]-benzothiazol-2-yl}-benzamide a) (2-Methoxy-ethyl)-(4-methoxy-phenyl)-methyl-amine To a stirred solution of 1.00 g (7.29 mmol) N-methyl-p-anisidine in 15 ml acetonitrile at 0° C. were added dropwise 1.36 ml (8.02 mmol) N-ethyldiisopropylamine and 1.01 g (7.29 mmol) 2-bromoethyl methyl ether. The mixture was heated at 80° C. for 2 days and then concentrated in vacuo. Flash chromatography (1/9 ethyl acetate/hexane) afforded 1.20 g (84%) (2-methoxy-ethyl)-(4-methoxy-phenyl)-methyl-amine as an orange oil. ES-MS m/e (%): 196 (M+H$^+$, 100).

b) (2-Methoxy-ethyl)-(4-methoxy-3-nitro-phenyl)-methyl-amine

To a stirred solution of 600 mg (3.07 mmol) (2-methoxy-ethyl)-(4-methoxy-phenyl)-methyl-amine in 1.3 ml concentrated sulfuric acid at room temperature was added 222 mg (3.69 mmol) urea. After stirring for 1 h at room temperature, a solution of 342 mg (3.38 mmol) potassium nitrate in 0.6 ml concentrated sulfuric acid was added dropwise and stirring continued for a further 16 h. The mixture was then poured onto water amd extracted five times with dichloromethane. The combined organic phases were dried over sodium sulfate and concentrated in vacuo. Flash chromatography (1/9 ethyl acetate/hexane) afforded 260 mg (35%) (2-methoxy-ethyl)-(4-methoxy-3-nitro-phenyl)-methyl-amine as an orange oil. ES-MS m/e (%): 241 (M+H$^+$, 100).

c) 4-Methoxy-N1-(2-methoxy-ethyl)-N1-methyl-benzene-1,3-diamine

To a stirred solution of 2.50 g (10.4 mmol) (2-methoxy-ethyl)-(4-methoxy-3-nitro-phenyl)-methyl-amine in 100 ml methanol was added a spatula end of 10% palladium on charcoal and the mixture was then stirred for 16 hours at room temperature under an atmosphere of hydrogen. The mixture was then filtered and the filtrate concentrated in vacuo to afford 1.90 g (87 (ho) 4-methoxy-N1-(2-methoxy-ethyl)-N1-methyl-benzene-1,3-diamine as an off-white crystalline solid. ES-MS m/e (%): 211 (M+H$^+$, 100).

d) 1-Benzoyl-3-{2-methoxy-5-[(2-methoxy-ethyl)-methyl-amino]-phenyl}-thiourea

To a stirred solution of 1.89 g (8.99 mmol) 4-methoxy-N1-(2-methoxy-ethyl)-N1-methyl-benzene-1,3-diamine in 60 ml acetone was added dropwise a solution of 1.38 ml (10.3 mmol) benzoyl isothiocyanate in 30 ml acetone and stirring continued at room temperature for 30 minutes. The mixture was then concentrated in vacuo. Trituration in ether afforded 2.05 g (61%) 1-benzoyl-3-{2-methoxy-5-[(2-methoxy-ethyl)-methyl-amino]-phenyl}-thiourea as a yellow solid. ES-MS m/e ((Y)): 374 (M+H$^+$, 100).

e) N-{4-Methoxy-7-[(2-methoxy-ethyl)-methyl-amino]-benzothiazol-2-yl}-benzamide

To a stirred solution of 430 mg (1.15 mmol) 1-benzoyl-3-{2-methoxy-5-[(2-methoxy-ethyl)-methyl-amino]-phenyl}-thiourea in 8 ml chloroform was added dropwise 0.059 ml (1.15 mmol) bromine and the reaction mixture heated at reflux for 18 hours. The mixture was then cooled to room temperature, poured slowly onto water and extracted three times with ethyl acetate. The combined organic phases were dried over sodium sulfate and concentrated in vacuo. Flash chromatography (1/4 ethyl acetate/hexane) afforded 120 mg (28%) N-{4-methoxy-7-[(2-methoxy-ethyl)-methyl-amino]-benzothiazol-2-yl}-benzamide as a yellow solid. ES-MS m/e (%): 394 (M+Na$^+$, 14), 372 (M+H$^+$, 100).

EXAMPLE 2

4-Fluoro-N-{4-methoxy-7-[(2-methoxy-ethyl)-methyl-amino]-benzothiazol-2-yl}-benzamide a) {2-Methoxy-5[-(2-methoxy-ethyl)-methyl-amino]-pheny}-thiourea To a stirred suspension of 2.00 g (5.36 mmol) 1-benzoyl-3-{2-methoxy-5-[(2-methoxy-ethyl)-methyl-amino]-phenyl}-thiourea in 13 ml methanol was added dropwise 0.15 ml (0.80 mmol) 5.4 M sodium methylate solution and stirring continued for 1 h at room temperature. The mixture was then poured onto water and extracted three times with ethyl acetate. The combined organic phases were dried over sodium sulfate and concentrated in vacuo. Flash chromatography (ethyl acetate) afforded 1.40 g (97%) {2-methoxy-5-[(2-methoxy-ethyl)-methyl-amino]-phenyl}-thiourea as an amber oil. ES-MS m/e (%): 270 (M+H+, 100).

b) 4-Methoxy-N7-(2-methoxy-ethyl)-N7-methyl-benzothiazole-2,7-diamine

To a stirred solution of 1.40 g (5.20 mmol) {2-methoxy-5-[(2-methoxy-ethyl)-methyl-amino]-phenyl}-thiourea in 35 ml chloroform was added dropwise 0.27 ml (5.27 mmol) bromine and the reaction mixture heated at reflux for 18 hours. The mixture was then cooled to room temperature, poured slowly onto sodium bicarbonate solution and extracted three times with ethyl acetate. The combined organic phases were dried over sodium sulfate and concentrated in vacuo. Flash chromatography (ethyl acetate) afforded 984 mg (71%) 4-methoxy-N7-(2-methoxy-ethyl)-N7-methyl-benzothiazole-2,7-diamine as an orange crystalline solid. ES-MS m/e (%): 268 (M+H$^+$, 100).

c) 4-Fluoro-N-{4-methoxy-7-[(2-methoxy-ethyl)-methyl-amino]-benzothiazol-2-yl}-benzamide To a stirred solution of 79 mg (0.56 mmol) 4-fluoro-benzoic acid in 10 ml THF were added 235 mg (0.62 mmol) HATU and 0.11 ml (0.62 mmol) N-ethyldiisopropylamine and stirring continued at room temperature for 1 h. A solution of 150 mg (0.56 mmol) 4-methoxy-N7-(2-methoxy-ethyl)-N7-methyl-benzothiazole-2,7-diamine in 5 ml dioxane and 1 ml DMF was then added and stirring continued at room temperature for 16 h. The reaction mixture was then poured into 100 ml 1 M hydrochloric acid and extracted three times with dichloromethane. The combined organic phases were dried over sodium sulfate and concentrated in vacuo. Flash chromatography (1/4-1/1 ethyl acetate/hexane) followed by trituration in hexane afforded 55 mg (25%) 4-fluoro-N-{4-methoxy-7-[(2-methoxy-ethyl)-methyl-amino]-benzothiazol-2-yl}-benzamide as an off-white crystalline solid. ES-MS m/e (%): 390 (M+H$^+$, 100).

EXAMPLE 3

4-Chloromethyl-N-{4-methoxy-7-[(2-methoxy-ethyl)-methyl-amino]-benzothiazol-2-yl}-benzamide To a stirred solution of 300 mg (1.12 mmol) 4-methoxy-N7-(2-methoxy-ethyl)-N7-methyl-benzothiazole-2,7-diamine and 1.12 ml (6.56 mmol) N-ethyldiisopropylamine in 10 ml THF at room temperature was added dropwise a solution of 257 mg (1.36 mmol) 4-(chloromethyl)-benzoyl chloride in 3 ml dichloromethane and stirring continued at room temperature for 16 h. The reaction mixture was then concentrated in vacuo. Flash chromatography (1/1 ethyl acetate/hexane) followed by trituration in ether and hexane afforded 200 mg (42%) 4-chloromethyl-N-{4-methoxy-7-[(2-methoxy-ethyl)-methyl-amino]-benzothiazol-2-yl}-benzamide as a light yellow crystalline solid. ES-MS m/e (%): 422 (M{$^{37}$Cl}+H$^+$, 32), 420 (M{$^{35}$Cl}+H$^+$, 100).

Analogously to Example 2 there were obtained:

EXAMPLE 4

N-{4-Methoxy-7-[(2-methoxy-ethyl)-methyl-amino]-benzothiazol-2-yl}-2-methyl-isonicotinamide From 2-methyl-isonicotinic acid hydrochloride, HATU and N-diethylisopropylamine in THF, then treatment with 4-methoxy-N7-(2-methoxy-ethyl)-N7-methyl-benzothiazole-2,7-diamine in dioxane and DMF. ES-MS m/e (%): 387 (M+H$^+$, 100).

EXAMPLE 5

2-Bromo-N-{4-methoxy-7-[(2-methoxy-ethyl)-methyl-amino]-benzothiazol-2-yl}-isonicotinamide From 2-bromo-isonicotinic acid, HATU and N-diethylisopropylamine in THF, then treatment with 4-methoxy-N7-(2-methoxy-ethyl)-N7-methyl-benzothiazole-2,7-diamine in dioxane and DMF. ES-MS m/e (%): 453 (M{$^{81}$Br}+H$^+$, 100), 451 (M{$^{79}$Br}+H$^+$, 71).

EXAMPLE 6

N-{4-Methoxy-7-[(2-methoxy-ethyl)-methyl-amino]-benzothiazol-2-yl}-2-morpholin-4-yl-isonicotinamide A stirred suspension of 200 mg (0.44 mmol) 2-bromo-N-{4-methoxy-7-[(2-methoxy-ethyl)-methyl-amino]-benzothiazol-2-yl}-isonicotinamide, 0.38 ml (4.43 mmol) morpholine and 289 mg (0.89 mmol) cesium carbonate in 5 ml N-methylpyrrolidone in a thick-walled glass pressure tube fitted with a teflon cap was heated at 140° C. for 24 h. The reaction mixture was then cooled to room temperature and poured onto water. The mixture was extracted three times with ethyl acetate, and the combined organic phases were dried over sodium sulfate and concentrated in vacuo. Flash chromatography (ethyl acetate) followed by trituration in ether afforded 100 mg (49%) N-{4-methoxy-7-[(2-methoxy-ethyl)-methyl-amino]-benzothiazol-2-yl}-2-morpholin-4-yl-isonicotinamide as a light yellow crystalline solid. ES-MS m/e (%): 458 (M+H$^+$, 100).

EXAMPLE 7

N-[4-Methoxy-7-{(1S,4S)-(2-oxa-5-aza-bicyclo[2.2.1]hept-5-yl)}-benzothiazol-2-yl]-2-methyl-isonicotinamide a) (1S,4S)-5-(4-Methoxy-3-nitro-phenyl)-2-oxa-5-aza-bicyclo[2.2.1]heptane To a stirred solution of 7.34 g (31.0 mmol) 4-bromo-2-nitro-anisole in 125 ml dioxane were added 5.25 g (37.2 mmol) (1S,4S)-(+)-2-aza-5-oxabicyclo[2,2,1]heptane hydrochloride, 1.109 g (3.10 mmol) 2-(dicyclohexylphosphino)biphenyl, 14.2 g (43.4 mmol) cesium carbonate, 696 mg (3.10 mmol) palladium (II) acetate and 5.65 ml (40.3 mmol) triethylamine. The mixture was heated at reflux for 24 h and then poured onto water and extracted three times with ethyl acetate. The combined organic phases were dried over sodium sulfate and concentrated in vacuo. Flash chromatography (1/99 methanol/dichloromethane) afforded 5.10 g (66%) (1S,4S)-5-(4-methoxy-3-nitro-phenyl)-2-oxa-5-aza-bicyclo[2.2.1]heptane as an orange oil. ES-MS m/e (%): 251 (M+H$^+$, 100).

b) 2-Methoxy-5-{(1S,4S)-(2-oxa-5-aza-bicyclo[2.2.1]hept-5-yl)}-phenylamine

To a stirred solution of 5.01 g (20.0 mmol) (1S,4S)-5-(4-methoxy-3-nitro-phenyl)-2-oxa-5-aza-bicyclo[2.2.1]heptane in 375 ml methanol and 62.5 ml dichloromethane was added 500 mg 10% palladium on charcoal and the mixture was then stirred for 3.5 hours at room temperature under an atmosphere of hydrogen. The mixture was then filtered and the filtrate concentrated in vacuo to afford 4.30 g (98%) 2-methoxy-5-{(1S,4S)-(2-oxa-5-aza-bicyclo[2.2.1]hept-5-yl)}-phenylamine as a brown crystalline solid. ES-MS m/e (%): 221 (M+H$^+$, 100).

c) 1-Benzoyl-3-[2-methoxy-5-{(1S,4S)-(2-oxa-5-aza-bicyclo[2.2.1]hept-5-yl)}-phenyl]-thiourea To a stirred solution of 4.20 g (19.1 mmol) 2-methoxy-5-{(1S,4S)-(2-oxa-5-aza-bicyclo[2.2.1]hept-5-yl)}-phenylamine in 200 ml acetone was added dropwise 2.88 ml (21.0 mmol) benzoyl isothiocyanate and stirring continued for 1 h at room temperature. The mixture was then concentrated in vacuo to afford 7.30 g (100%) 1-benzoyl-3-[2-methoxy-5-{(1S,4S)-(2-oxa-5-aza-bicyclo[2.2.1]hept-5-yl)

}-phenyl]-thiourea as a yellow solid. ES-MS m/e (%): 406 (M+Na+, 13), 384 (M+H+, 100).

d) [2-Methoxy-5-{(1S,4S)-(2-oxa-5-aza-bicyclo[2.2.1]hept-5-yl)}-phenyl]-thiourea To a stirred suspension of 7.25 g (18.9 mmol) 1-benzoyl-3-[2-methoxy-5-{(1S,4S)-(2-oxa-5-aza-bicyclo[2.2.1]hept-5-yl)}-phenyl]-thiourea in 350 ml methanol was added dropwise 7.02 ml (37.8 mmol) 5.4 M sodium methylate solution and stirring continued for 1 h at room temperature. The resulting crystals were collected by filtration to afford 3.42 g (65%) [2-methoxy-5-{(1S,4S)-(2-oxa-5-aza-bicyclo[2.2.1]hept-5-yl)}-phenyl]-thiourea as a beige solid. ES-MS m/e (%):302 (M+Na+, 20), 281 (M+H+, 100).

e) 4-Methoxy-7-{(1S,4S)-(2-oxa-5-aza-bicyclo[2.2.1]hept-5-yl)}-benzothiazol-2-ylamine To a stirred solution of 279 mg (1.00 mmol) [2-methoxy-5-{(1S,4S)-(2-oxa-5-aza-bicyclo[2.2.1]hept-5-yl)}-phenyl]-thiourea in 8 ml chloroform at room temperature was added dropwise 0.051 ml (1.00 mmol) bromine and the mixture heated at reflux for 24 h. The mixture was then concentrated in vacuo and the residue suspended in water. Sodium bicarbonate solution was added until the pH was 10, and the crystals were collected by filtration. Flash chromatography (5/95 methanol/dichloromethane) afforded 91.5 mg (33%) 4-methoxy-7-{(1S,4S)-(2-oxa-5-aza-bicyclo[2.2.1]hept-5-yl)}-benzothiazol-2-ylamine as an off-white crystalline solid. ES-MS m/e (%): 278 (M+H+, 100).

f) N-[4-Methoxy-7-{(1 S,4S)-(2-oxa-5-aza-bicyclo[2.2.1]hept-5-yl)}-benzothiazol-2-yl]-2-methyl-isonicotinamide To a stirred solution of 111 mg (0.40 mmol) 4-methoxy-7-{(1S,4S)-(2-oxa-5-aza-bicyclo[2.2.1]hept-5-yl)}-benzothiazol-2-ylamine and 0.26 ml (1.50 mmol) N-ethyldiisopropylamine in 20 ml THF at room temperature was added dropwise a solution of 127 mg (0.66 mmol) 2-methyl-isonicotinoyl chloride hydrochloride in 20 ml dichloromethane and stirring continued at room temperature for 24 h. The reaction mixture was then concentrated in vacuo. Flash chromatography (3/97 methanol/ethyl acetate) followed by trituration in ether afforded 142 mg (90%) N-[4-methoxy-7-{(1S,4S)-(2-oxa-5-aza-bicyclo[2.2.1]hept-5-yl)}-benzothiazol-2-yl]-2-methyl-isonicotinamide as a yellow crystalline solid. ES-MS m/e (%): 419 (M+Na+, 17), 397 (M+H+, 100).

EXAMPLE 8

{4-Methoxy-7-[(pyridin-2-ylmethyl)-amino]-benzothiazol-2-yl}-carbamic Acid Methyl Ester a) (4-Methoxy-benzothiazol-2-yl)-carbamic acid methyl ester To a stirred solution of 23.6 g (131 mmol) 2-amino-4-methoxybenzothiazole and 12.6 ml (157 mmol) pyridine in 230 ml dichloromethane at 0° C. was added dropwise 10.6 ml (137 mmol) methyl chloroformate and stirring continued for 1 hour. The mixture was then poured onto 1 M hydrochloric acid and the organic phase was separated, washed with brine, dried over sodium sulfate, and concentrated in vacuo to afford 31.0 g (99%) (4-methoxy-benzothiazol-2-yl)-carbamic acid methyl ester as a white solid. ES-MS m/e (%): 239 (M+H+, 100).

b) (4-Methoxy-7-nitro-benzothiazol-2-yl)-carbamic Acid Methyl Ester

To a stirred solution of 13.6 g (57.1 mmol) (4-methoxy-benzothiazol-2-yl)-carbamic acid methyl ester in 300 ml acetic acid at room temperature was added 200 ml 65% nitric acid and the mixture heated at 70° C. for 4 h. The mixture was then poured onto stirred ice-water and the resulting slurry was filtered. The filter-cake was dissolved in THF and 5 N sodium hydroxide solution was added until the pH was 8. This mixture was then stirred for 1 h, filtered, and the filter-cake dried in vacuo to afford 7.61 g (47%) (4-methoxy-7-nitro-benzothiazol-2-yl)-carbamic acid methyl ester as a yellow crystalline solid. Meanwhile, the filtrate was separated into its aqueous and organic phases and the organic phase was dried over sodium sulfate and concentrated in vacuo. The residue was resuspended in 200 ml THF and 200 ml methanol and heated at 70° C. overnight. The mixture was then cooled to room temperature and the resulting crystals were collected by filtration, washed with THF, and dried in vacuo to afford a further 1.50 g (9%) of product as a yellow crystalline solid. ES-MS m/e (%): 306 (M+Na+, 28), 2,S4 (M+H+, 100).

c) (7-Amino-4-methoxy-benzothiazol-2-yl)-carbamic Acid Methyl Ester

To a stirred solution of 5.00 g (17.7 mmol) (4-methoxy-7-nitro-benzothiazol-2-yl)-carbamic acid methyl ester in 140 ml methanol and 140 ml dichloromethane was added 1.5 g platinum (IV) oxide and the mixture was then stirred for 16 hours at room temperature under an atmosphere of hydrogen. The mixture was then filtered and the filtrate concentrated in vacuo to afford 4.03 g (90%) (7-amino-4-methoxy-benzothiazol-2-yl)-carbamic acid methyl ester as a grey crystalline solid. ES-MS m/e (%):276 (M+Na+, 28), 254 (M+H+, 100).

d) {14-Methoxy-7-[(pyridin-2-ylmethyl)-amino]-benzothiazol-2-yl}-carbamic Acid Methyl Ester To a stirred solution of 40 mg (0.16 mmol) (7-amino-4-methoxy-benzothiazol-2-yl)-carbamic acid methyl ester in 2 ml DM F at room temperature were added 66 mg (0.47 mmol) potassium carbonate and 40 mg (0.16 mmol) 2-(bromomethyl)pyridine hydrobromide and the mixture heated at 70° C. for 16 h. The mixture was then concentrated in vacuo. Flash chromatography (2/1 ethyl acetate/hexane) afforded 20 mg (37%) {4-methoxy-7-[(pyridin-2-ylmethyl)-amino]-benzothiazol-2-yl}-carbamic acid methyl ester as a yellow solid. ES-MS m/e (%): 367 (M+Na+, 54), 345 (M+H+, 100).

EXAMPLE 9

N-[4-Methoxy-7-(4-methyl-benzylamino)-benzothiazol-2-yl]-benzamide
and

EXAMPLE 10

N-{7-[Acetyl-(4-methyl-benzyl)-amino]-4-methoxy-benzothiazol-2-yl}-benzamide a) 4-Methoxy-3-nitro-phenylamine To a stirred solution of 30.0 g (244 mmol) p-anisidine in 105 ml concentrated sulfuric acid at 0° C. was added 17.6 g (292 mmol) urea. After stirring for 1 h, a solution of 27.1 g (268 mmol) potassium nitrate in 47 ml concentrated sulfuric acid was then added dropwise over 1 h while the reaction mixture was maintained at 5–10° C. The mixture was then poured onto ice, and sodium hydroxide pellets added portionwise with stirring until the pH was 14. Ethyl acetate was then added and the phases were separated. The organic phase was washed with water and then with brine, dried over sodium sulfate, and concentrated in vacuo to afford 31.4 g (77%) 4-methoxy-3-nitro-phenylamine as an orange solid. EI-MS m/e (%): 169 (M+, 100), 153 ([M-CH$_3$]+, 10), 92 (21).

b) (4-Methoxy-3-nitro-phenyl)-bis-(4-methyl-benzyl)-amine

To a stirred solution of 5.00 g (29.7 mmol) 4-methoxy-3-nitro-phenylamine in 60 ml acetonitrile at 0° C. were added 10.2 ml (59.5 mmol) N-ethyldiisopropylamine and 11.6 g (62.4 mmol) 4-methylbenzyl bromide. Stirring was continued at room temperature for 16 h and then the mixture was diluted with ethyl acetate and washed with 0.5 N hydrochloric acid and then with brine. The organic phase was dried over sodium sulfate and concentrated in vacuo to afford 10.4 g (93%) (4-methoxy-3-nitro-phenyl)-bis-(4-methyl-benzyl)-amine as an orange oil. ES-MS m/e (%): 399 (M+Na+, 18), 377 (M+H$^+$, 100).

c) 4-Methoxy-N1,N1-bis-(4-methyl-benzyl)-benzene-1,3-diamine

To a stirred solution of 500 mg (1.33 mmol) (4-methoxy-3-nitro-phenyl)-bis-(4-methyl-benzyl)-amine in 20 ml ethanol at room temperature were added 1.91 g (29.2 mmol) zinc powder and 147 mg (1.33 mmol) calcium chloride and the mixture was then heated at 90° C. for 16 hours. The mixture was then filtered and the filtrate diluted with ethyl acetate and washed with 0.5 N sodium hydroxide solution and then with brine. The organic phase was dried over sodium sulfate and concentrated in vacuo to afford 420 mg (91%) 4-methoxy-N1,N1-bis-(4-methyl-benzyl)-benzene-1,3-diamine as a dark brown oil. ES-MS m/e (%): 347 (M+H$^+$, 100).

d) 1-Benzoyl-3-{5-[bis-(4-methyl-benzyl)-amino]-2-methoxy-phenyl}-thiourea

To a stirred solution of 400 mg (1.15 mmol) 4-methoxy-N1,N1-bis-(4-methyl-benzyl)-benzene-1,3-diamine in 8 ml acetone was added dropwise a solution of 0.18 ml (1.34 mmol) benzoyl isothiocyanate in 4 ml acetone and stirring continued for 30 minutes at room temperature. The mixture was then diluted with ethyl acetate and washed with water and then with brine. The organic phase was dried over sodium sulfate and concentrated in vacuo. Flash chromatography (1/9 ethyl acetate/hexane) afforded 320 mg (80%) 1-benzoyl-3-{5-[bis-(4-methyl-benzyl)-amino]-2-methoxy-phenyl}-thiourea as a yellow oil. ES-MS m/e (%): 510 (M+H$^+$, 100).

e) N-{7-[Bis-(4-methyl-benzyl)-amino]-4-methoxy-benzothiazol-2-yl}-benzamide

To a stirred solution of 500 mg (0.98 mmol) 1-benzoyl-3-{5-[bis-(4-methyl-benzyl)-amino]-2-methoxy-phenyl}-thiourea in 7 ml chloroform was added dropwise 0.050 ml (0.98 mmol) bromine and the reaction mixture heated at reflux for 18 hours. The mixture was then diluted with ethyl acetate and washed with water and then with brine. The organic phase was dried over sodium sulfate and concentrated in vacuo. Flash chromatography (ethyl acetate/hexane) afforded 290 mg (58%) N-{7-[bis-(4-methyl-benzyl)-amino]-4-methoxy-benzothiazol-2-yl}-benzamide as a yellow solid. ES-MS m/e (%): 394 (M+Na$^+$, 14), 508 (M+H$^+$, 100).

f) (2-Benzoylamino-4-methoxy-benzothiazol-7-yl)-(4-methyl-benzyl)-carbamic acid 2,2,2-trichloro-ethyl Ester To a stirred solution of 300 mg (0.59 mmol) N-{7-[bis-(4-methyl-benzyl)-amino]-4-methoxy-benzothiazol-2-yl}-benzamide in 10 ml acetonitrile was added dropwise 0.60 ml (4.46 mmol) 2,2,2-trichloroethyl chloroformate and the reaction mixture heated at 80° C. for 72 h. The mixture was then concentrated in vacuo. Flash chromatography (ethyl acetate/hexane) afforded 138 mg (40%) (2-benzoylamino-4-methoxy-benzothiazol-7-yl)-(4-methyl-benzyl)-carbamic acid 2,2,2-trichloro-ethyl ester as a yellow solid. ES-MS m/e (%):584 (M{$^{37}$Cl, $^{37}$Cl, $^{37}$Cl}+H$^+$, 5), 582 (M{$^{37}$Cl, $^{37}$Cl, $^{35}$Cl}+H$^+$, 32), 580 (M{$^{37}$Cl, $^{35}$Cl, $^{35}$Cl}+H$^+$, 100), 578 (M{$^{35}$Cl, $^{35}$Cl, $^{35}$Cl}+H$^+$, 92).

g) N-[4-Methoxy-7-(4-methyl-benzylamino)-benzothiazol-2-yl]-benzamide and N-{7-[Acetyl-(4-methyl-benzyl)-amino]-4-methoxy-benzothiazol-2-yl}-benzamide To a stirred solution of 100 mg (01.17 mmol) (2-benzoylamino-4-methoxy-benzothiazol-7-yl)-(4-methyl-benzyl)-carbamic acid 2,2,2-trichloro-ethyl ester in 3 ml acetic acid at room temperature was added 90 mg (1.34 mmol) activated zinc powder and the mixture was heated at 80° C. for 16 hours. The mixture was then filtered and the filtrate concentrated in vacuo. Flash chromatography (ethyl acetate/hexane) afforded 15 mg (21%) N-[4-methoxy-7-(4-methyl-benzylamino)-benzothiazol-2-yl]-benzamide as a yellow crystalline solid, ES-MS m/e (%): 426 (M+Na$^+$, 27), 404 (M+H$^+$, 100), and 10 mg (13%) N-{7-[acetyl-(4-methyl-benzyl)-amino]-4-methoxy-benzothiazol-2-yl}-benzamide as a yellow crystalline solid, ES-MS m/e (%): 468 (M+Na$^+$, 12), 446 (M+H$^+$, 100).

EXAMPLE 11

4-{[(2-Methoxy-ethyl)-methyl-amino]-methyl}-N-{4-methoxy-7-[(2-methoxy-ethyl)-methyl-amino]-benzothiazol-2-yl}-benzamide Dihydrochloride A mixture of 100 mg (0.24 mmol) 4-chloromethyl-N-{4-methoxy-7-[(2-methoxy-ethyl)-methyl-amino]-benzothiazol-2-yl}-benzamide and 212 mg (2.38 mmol) N-(2-methoxyethyl)methylamine was ultrasonicated at room temperature for 30 minutes. The reaction mixture was then concentrated it vactio and the residue purified by flash chromatography (ethyl acetate). The product-containing fractions were concentrated in vactio and the residue stirred with HCl in ether and ethyl acetate. The resulting crystals were collected by filtration and washed with ether to afford 110 mg (91%) 4-{[(2-methoxy-ethyl)-methyl-amino]-methyl}-N-{4-methoxy-7-[(2-methoxy-ethyl)-methyl-amino]-benzothiazol-2-yl}-benzamide dihydrochloride as a white crystalline solid. ES-MS m/e (%): 473 (M+H$^+$, 100).

EXAMPLE 12

N-(7-Dimethylamino-4-methoxy-benzothiazol-2-yl)-4-fluoro-benzamide a) 4-Methoxy-benzothiazole-2,7-diamine To a suspension of 4.28 g (16.9 mmol) (7-amino-4-methoxy-benzothiazol-2-yl)-carbamic acid methyl ester in 100 ml dioxane and 50 ml ethylene glycol was added 100 ml 5 N NaOH and the mixture was heated at 100° C. for 16 h. After cooling to room temperature, the reaction mixture was concentrated in vacuo and the residue diluted with 300 ml tetrahydrofuran and stirred for 10 minutes. The mixture was filtered and the filtrate concentrated in vactio. The residue was triturated in ether to afford 2.73 g (83%) 4-methoxy-benzothiazole-2,7-diamine as a brown solid. ES-MS m/e (%): 196 (M+H$_+$, 100). b) 4-Methoxy-N7,N7-dimethyl-benzothiazole-2,7-diamine To a stirred solution of 2.00 g (1.02 mmol) 4-methoxy-benzothiazole-2,7-diamine in 30 ml DMF at room temperature was added 4.25 g (3.07 mmol) potassium carbonate and the mixture heated to 50° C. A solution of 0.64 ml (1.02 mmol) iodomethane in 10 ml DMF was then added dropwise over 3 h and stirring continued for a further 1 h at 50° C. The mixture was then filtered and the filtrate concentrated in vacuo. Flash chromatography (20/1 dichloromethane/methanol) afforded 600 mg (26%) 4-methoxy-N7,N7-dimethyl-benzothiazole-2,7-diamine as a yellow solid, ES-MS m/e (%): 224 (M+H$^+$, 100); 540 mg (25%) 4-methoxy-N7-methyl-benzothiazole-2,7-diamine as a yellow solid, ES-MS m/e (%): 210 (M+H$^+$, 100) and 340 mg (17%) recovered starting material.

c) N-(7-Dimethylamino-4-methoxy-benzothiazol-2-yl)-4-fluoro-benzamide

To a stirred solution of 41 mg (0.29 mmol) 4-fluoro-benzoic acid in 1 ml THF were added 128 mg (0.34 mmol) HATU and 0.10 ml (0.56 mmol) N-ethyldiisopropylamine and stirring continued at room temperature for 2.5 h. 50 mg (0.22 mmol) 4-methoxy-N7,N7-dimethyl-benzothiazole-2,7-diamine was then added and stirring continued at room temperature for 16 h. The reaction mixture was then concentrated in vactio. Flash chromatography (ethyl acetate/hexane) afforded 64 mg (83%) N-(7-dimethylamino-4-methoxy-benzothiazol-2-yl)-4-fluoro-benzamide as a white crystalline solid. ES-MS m/e (%): 346 (M+H $^+$, 100).

In an analogous manner there were obtained:

EXAMPLE 13

N-(7-Diethylamino-4-methoxy-benzothiazol-2-yl)-4-fluoro-benzamide

From 4-methoxy-benzothiazole-2,7-diamine with potassium carbonate and iodoethane in DMF, then treatment with 4-fluoro-benzoic acid, HATU and N-ethyldiisopropylamine in THF. ES-MS m/e (%): 374 (M+H$^+$, 100).

EXAMPLE 14

N-[7-(Benzyl-methyl-amino)-4-methoxy-benzothiazol-2-yl]-4-fluoro-benzamide

From 4-methoxy-N7-methyl-bentzothiazole-2,7-diamine with potassium carbonate and benzyl bromide in DMF, then treatment with 4-fluoro-benzoic acid, HATU and N-ethyldiisopropylamine in THF. ES-MS m/e (%): 422 (M+H$^+$, 100).

EXAMPLE 15

4-Fluoro-N-[4-methoxy-7-(methyl-pyridin-2-ylmethyl-amino)-benzothiazol-2-yl]-benzamide From 4-methoxy-N7-methyl-benzothiazole-2,7-diamine with potassium carbonate and 2-(bromomethyl)pyridine hydrobromide in DMF, then treatment with 4-fluoro-benzoic acid, HATU and N-ethyldiisopropylamine in THF. ES-MS m/e (%): 423 (M+H$^+$, 100).

EXAMPLE 16

N-[7-(Benzyl-methyl-amino)-4-methoxy-benzothiazol-2-yl]-2-methyl-isonicotinamide From 4-methoxy-N7-methyl-benzothiazole-2,7-diamine with potassium carbonate and benzyl bromide in DMF, then treatment with 2-methyl-isonicotinic acid hydrochloride, HATU and N-ethyldiisopropylamine in THF. ES-MS m/e (%): 419 (M+H$^+$, 100).

EXAMPLE 17

N-[7-(Dimethylcarbamoylmethyl-methyl-amino)-4-methoxy-benzothiazol-2-yl]-4-fluoro-benzamide From 4-methoxy-N7-methyl-benzothiazole-2,7-diamine with potassium carbonate and 2-iodo-N,N-dimethyl-acetamide in DMF, then treatment with 4-fluorobenzoic acid, HATU and N-ethyldiisopropylamine in THF. ES-MS m/e (%): 417 (M+H$_+$, 100).

EXAMPLE 18

N-(7-Diethylamino-4-methoxy-benzothiazol-2-yl)-2-methyl-isonicotinamide

From 4-methoxy-benzothiazole-2,7-diamine with potassium carbonate and iodoethane in DMF, then treatment with 2-methyl-isonicotinic acid hydrochloride, HATU and N-ethyldiisopropylamine in THF. ES-MS m/e (%): 371 (M+H$^+$, 100).

EXAMPLE 19

N-[7-(Acetyl-methyl-amino)-4-methoxy-benzothiazol-2-yl]-4-fluoro-benzamide a) N-(2-Amino-4-methoxy-benzothiazol-7-yl)-N-methyl-acetamide To a stirred solution of 120 mg (0.57 mmol) 4-methoxy-N7-methyl-benzothiazole-2,7-diamine in 1 ml dichloromethane and 1 ml tetrahydrofuran at 0° C. was added 0.09 ml (1.15 mmol) pyridine. A solution of 0.04 ml (0.57 mmol) acetyl chloride in 1 ml dichloromethane was then added dropwise and stirring continued for 3 h at 0° C. The mixture was then concentrated in vacuo. Flash chromatography (30/1 dichloromethane/methanol) afforded 60 mg (42%) N-(2-amino-4-methoxy-benzothiazol-7-yl)-N-methyl-acetamide as a light brown crystalline solid, ES-MS m/e (%): 252 (M+H$_+$, 100).

b) N-[7-(Acetyl-methyl-amino)-4-methoxy-benzothiazol-2-yl]-4-fluoro-benzamide

To a stirred solution of 31 mg (0.22 mmol) 4-fluoro-benzoic acid in 2 ml THF were added 89 mg (0.23 mmol) HATU and 0.07 ml (0.44 mmol) N-ethyldiisopropylamine and stirring continued at room temperature for 2 h. 28 mg (0.11 mmol) N-(2-amino-4-methoxy-benzothiazol-7-yl)-N-methyl-acetamide was then added and stirring continued at 50° C. for 16 h. The reaction mixture was then concentrated in vacuo. Flash chromatography (dichloromethane/methanol 50/1) followed by trituration in ether afforded 10 mg (24%) N-[7-(acetyl-methyl-amino)-4-methoxy-benzothiazol-2-yl]-4-fluoro-benzamide as a white crystalline solid. ES-MS m/e (%o): 374 (M+H$^+$, 100).

Analogously to Example 12 there was obtained:

EXAMPLE 20

N-[7-(Dimethylcarbamoylmethyl-ethyl-amino)-4-methoxy-benzothiazol-2-yl]-4-fluoro-benzamide From N7-ethyl-4-methoxy-benzothiazole-2,7-diamine with potassium carbonate and 2-iodo-N,N-dimethyl-acetamide in DMF, then treatment with 4-fluorobenzoic acid, HATU and N-ethyldiisopropylamine in THF. ES-MS m/e (%): 431 (M+H$^+$, 100).

Analogously to Example 19 there were obtained:

EXAMPLE 21

N-[7-(Acetyl-ethyl-amino)-4-methoxy-benzothiazol-2-yl]-4-fluoro-benzamide

From N7-ethyl-4-methoxy-benzothiazole-2,7-diamine with pyridine and acetyl chloride in dichloromethane and THF, then treatment with 4-fluorobenzoic acid, HATU and N-methylmopholine in THF. ES-MS m/e (%): 388 (M+H$^+$, 100).

EXAMPLE 22

N-[7-(Acetyl-ethyl-amino)-4-methoxy-benzothiazol-2-yl]-2-methyl-isonicotinamide

From N7-ethyl-4-methoxy-benzothiazole-2,7-diamine with pyridine and acetyl chloride in dichloromethane and THF, then treatment with 2-methyl-isonicotinic acid hydrochloride, HATU and N-methylmopholine in THF. ES-MS m/e (%): 385 (M+H$^+$, 100).

Analogously to Example 12 there was obtained:

EXAMPLE 23

N-[7-(Benzyl-ethyl-amino)-4-methoxy-benzothiazol-2-yl]-4-fluoro-benzamide

From N7-ethyl-4-methoxy-benzothiazole-2,7-diamine with potassium carbonate and benzyl bromide in DMF, then treatment with 4-fluorobenzoic acid, HATU and N-ethyldiisopropylamine in THF. ES-MS m/e (%): 436 (M+H$^+$, 100).

Analogously to Example 19 there were obtained:

EXAMPLE 24

N-[7-(Acetyl-benzyl-amino)-4-methoxy-benzothiazol-2-yl]-4-fluoro-benzamide

From N7-benzyl-4-methoxy-benzothiazole-2,7-diamine with pyridine and acetyl chloride in dichloromethane and THF, then treatment with 4-fluorobenzoic acid, HATU and N-methylmopholine in THF. ES-MS m/e (%): 450 (M+H+, 100).

EXAMPLE 25
N-[7-(Acetyl-benzyl-amino)-4-methoxy-benzothiazol-2-yl]-2-bromo-isonicotinamide From N7-benzyl-4-methoxy-benzothiazole-2,7-diaminewith pyridine and acetyl chloride in dichloromethane and THF, then treatment with 2-bromo-isonicotinic acid, HATU and N-methylmopholine in THF. ES-MS m/e (%): 513 (M{$^{81}$Br}+H$^+$, 90), 511 (M{$^{79}$Br}+H$^+$, 100).

EXAMPLE 26
N-{7-[Acetyl-(2-methoxy-ethyl)-amino]-4-methoxy-benzothiazol-2-yl}-4-fluoro-benzamide From 4-methoxy-N7-(2-methoxy-ethyl)-benzothiazole-2,7-diamine with pyridine and acetyl chloride in dichloromethane and THF, then treatment with 4-fluoro-benzoic acid, HATU and N-methylmopholine in THF. ES-MS m/e (%): 418 (M+H$^+$, 90), 100).

EXAMPLE 27
N-{7-[Acetyl-(2-methoxy-ethyl)-amino]-4-methoxy-benzothiazol-2-yl}-2-bromo-isonicotinamide From 4-methoxy-N7-(2-methoxy-ethyl)-benzothiazole-2,7-diamine with pyridine and acetyl chloride in dichloromethane and THF, then treatment with 2-bromo-isonicotinic acid, HATU and N-methylmopholine in THF. ES-MS m/e (%): 481 (M{$^{81}$Br}+H$^+$, 100), 479 (M{$^{79}$Br}+H$^+$, 99).

EXAMPLE 28
4-Fluoro-N-{4-methoxy-7-[(4-methoxy-benzyl)-methyl-amino]-benzothiazol-2-yl}-benzamide From 4-methoxy-N7-methyl-benzothiazole-2,7-diamine with potassium carbonate and 4-methoxybenzyl chloride in DMF, then treatment with 4-fluorobenzoic acid, HATU and N-ethyldiisopropylamine in THF. ES-MS m/e (0/o): 452 (M+H$^+$, 100).

EXAMPLE 29
2-Bromo-N-{4-methoxy-7-[(4-methoxy-benzyl)-methyl-amino]-benzothiazol-2-yl}-isonicotinamide From 4-methoxy-N7-methyl-benzothiazole-2,7-diamine with potassium carbonate and 4-methoxybenzyl chloride in DMF, then treatment with 2-bromo-isonicotinic acid, HATU and N-ethyldiisopropylamine in THF. ES-MS m/e (%): 515 (M{$^{81}$Br}+H$^+$, 100), 513 (M{$^{79}$Br}+H$^+$, 81).

EXAMPLE 30
N-{4-Methoxy-7-[(4-methoxy-benzyl)-methyl-amino]-benzothiazol-2-yl}-2-methyl-isonicotinamide From 4-methoxy-N7-methyl-benizothiazole-2,7-diamine with potassium carbonate and 4-methoxybenzyl chloride in DMF, then treatment with 2-methyl-isonicotinic acid hydrochloride, HATU and N-ethyldiisopropylamine in THF. ES-MS m/e (%): 449 (M+H$^+$, 100).

EXAMPLE 31
4-Fluoro-N-{4-methoxy-7-[methyl-(2-oxo-2-piperidin-1-yl-ethyl)-amino]-benzothiazol-2-yl}-benzamide From 4-methoxy-benzothiazole-2,7-diamine with potassium carbonate and 2-iodo-1-morpholin-4-yl-ethanone in DMF, then treatment with potassium carbonate and iodomethane in DMF, then treatment with 4-fluorobenzoic acid, HATU and N-ethyldiisopropylamine in THF. ES-MS m/e (%): 457 (M+H$^+$, 100).

EXAMPLE 32
N-[7-(Benzyl-methyl-amino)-4-methoxy-benzothiazol-2-yl]-2-bromo-isonicotinamide From 4-methoxy-N7-methyl-benzothiazole-2,7-diamine with potassium carbonate and benzyl bromide in DMF, then treatment with 2-bromo-isonicotinic acid, HATU and N-ethyldiisopropylamine in THF. ES-MS m/e (%): 485 (M{$^{81}$Br}+H$^+$, 98), 483 (M{79Br}+H$^+$, 100).

EXAMPLE 33
2-Bromo-N-{4-methoxy-7-[methyl-(tetrahydro-pyran-4-ylmethyl)-amino]-benzothiazol-2-yl}-isonicotinamide a) (4-Methoxy-3-nitro-phenyl)-methyl-(tetrahydro-pyran-4-ylmethyl)-amine To a stirred solution of 4.70 g (20.0 mmol) 4-bromo-2-nitro-anisole in 100 ml dioxane were added 4.03 g (24.3 mmol) methyl-(tetrahydro-pyran-4-ylmethyl)-amine hydrochloride (1:1), 0.710 g (20.0 mmol) 2-(dicyclohexylphosphino)biphenyl, 16.5 g (50.65 mmol) cesium carbonate, and 227 mg (1.0 mmol) palladium (II) acetate. The mixture was heated at reflux for 24 h and then poured onto water and extracted three times with ethyl acetate. The combined organic phases were dried over sodium sulfate and concentrated in vacuo. Flash chromatography (1/1 hexane/ethyl acetate) afforded 3.5 g (62%) (4-methoxy-3-nitro-phenyl)-methyl-(tetrahydro-pyran-4-ylmethyl)-amine as a red oil. ES-MS m/e (%): 281 (M+H+, 100).

b) 4-Methoxy-N1-methyl-N1-(tetrahydro-pyran-4-ylmethyl)-benzene-1,3-diamine

To a stirred solution of 3.5 g (12.5 mmol) (4-methoxy-3-nitro-phenyl)-methyl-(tetrahydro-pyran-4-ylmethyl)-amine in 230 ml methanol was added 70 mg 10% palladium on charcoal and the mixture was then stirred for 18 hours at room temperature under an atmosphere of hydrogen. The mixture was then filtered and the filtrate concentrated in vacuo to afford 2.20 g (70%) 4-methoxy-N1-methyl-N1-(tetrahydropyran-4-ylmethyl)-benzene-1,3-diamine as a dark brown oil. ES-MS m/e (%): 251 (M+H$^+$, 100).

c) 1-Benzoyl-3-{2-methoxy-5-[methyl-(tetrahydro-pyran-4-ylmethyl)-amino]-phenyl}-thiourea To a stirred solution of 1.70 g (6.8 mmol) 4-methoxy-N1-methyl-N1-(tetrahydro-pyran-4-ylmethyl)-benzene-1,3-diamine in 30 ml acetone was added dropwise 1.0 ml (7.50 mmol) benzoyl isothiocyanate and stirring continued for 1 h at room temperature. The mixture was then concentrated in vacuo and the residue subjected to column chromatography (1/1 hexane/ethyl acetate) to afford 2.0 g (71%) 1-benzoyl-3-{2-methoxy-5-[methyl-(tetrahydro-pyran-4-ylmethyl)-amino]-phenyl}-thiourea as a yellow oil. ES-MS m/e (%): 436 (M+Na$^+$, 13), 414 (M+H$^+$, 100).

d) {2-Methoxy-5-[methyl-(tetrahydro-pyran-4-ylmethyl)-amino]-phenyl}-thiourea

To a stirred suspension of 2.0 g (4.8 mmol) 1-benzoyl-3-{2-methoxy-5-[methyl-(tetrahydro-pyran-4-ylmethyl)-amino]-phenyl}-thiourea in 15 ml methanol was added dropwise 0.4 ml (7.25 mmol) 5.4 M sodium methylate solution and stirring continued for 18 hrs at room temperature. The mixture was then concentrated in vactio and the residue subjected to column chromatography (1/1 hexane/ethyl acetate) to afford 1.5 g (100%) {2-methoxy-5-[methyl-(tetrahydro-pyran-4-ylmethyl)-amino]-phenyl}-thiourea as a beige oil. ES-MS m/e (%): 310 (M+H$^+$, 100).

e) 4-Methoxy-N7-methyl-N7-(tetrahydro-pyran-4-ylmethyl)-benzothiazole-2,7-diamine 1.5 g (0.53 mmol) {2-methoxy-5-[methyl-(tetrahydro-pyran-4-ylmethyl)-amino]-phenyl}-thiourea were dissolved in 15 ml chloroform and at room temperature 0.025 ml (0.5 mmol) Br$_2$ were added slowly. After 24 hrs of reflux the mixture was concentrated in vactio and the residue suspended in water. Sodium bicarbonate solution was added until the pH was 10, and the crystals were collected by filtration. These were subjected to column chromatography (1/1 hexane/ethyl acetate) to afford 0.16 g (10%) of 4-methoxy-N7-methyl-N7-(tetrahydro-pyran-4-ylmethyl)-benzothiazole-2,7-diamine as brown solid. ES-MS m/e (%): 308 (M+H$^+$, 100).

f) 2-Bromo-N-{4-methoxy-7-[methyl-(tetrahydro-pyran-4-ylmethyl)-amino]-benzothiazol-2-yl}-isonicotinamide To a stirred solution of 99 mg (0.49 mmol) 2-bromo-isonicotinic acid in 3 ml THF were added 195 mg (0.51 mmol) HATU and 0.11 ml (0.98 mmol) N-methylmorpholine and stirring continued at 30° C. for 5 h. 75 mg (0.24 mmol) 4-methoxy-N7-methyl-N7-(tetrahydro-pyran-4-ylmethyl)-benzothiazole-2,7-diamine was then added and stirring continued at 40° C. for 16 h. The reaction mixture was then diluted with ethyl acetate and washed sequentially with 0.5 N hydrochloric acid, saturated sodium bicarbonate solution and brine. The organic phase was dried over sodium sulfate and concentrated in vactio. Flash chromatography (methanol/dichloromethane) followed by trituration in ether/hexane afforded 17 mg (14%) 2-bromo-N-{4-methoxy-7-[methyl-(tetrahydro-pyran-4-ylmethyl)-amino)-benzothiazol-2-yl}-isonicotinamide as a white crystalline solid. ES-MS m/e (%): 493 (M{$^{81}$Br}+H$^+$, 100), 491 (M{$^{79}$Br}+H$^+$, 95).

In an analogous manner there was obtained:

EXAMPLE 34

4-Fluoro-N-{4-methoxy-7-[methyl-(tetrahydro-pyran-4-ylmethyl)-amino]-benzothiazol-2-yl}-benzamide From 4-methoxy-N7-methyl-N7-(tetrahydro-pyran-4-ylmethyl)-benzothiazole-2,7-diamine with 4-fluorobenzoic acid, HATU and N-ethyldiisopropylamine in THF. ES-MS m/e (%): 430 (M+H$^+$, 100).

Analogously to Example 6 there were obtained:

EXAMPLE 35

N-[7-(Benzyl-methyl-amino)-4-methoxy-benzothiazol-2-yl]-2-morpholin-4-yl-isonicotinamide From N-[7-(benzyl-methyl-amino)-4-methoxy-benzothiazol-2-yl]-2-bromo-isonicotinamide with morpholine and cesium carbonate. ES-MS m/e (%): 490 (M+H$^+$, 100).

EXAMPLE 36

2-Bromo-N-{4-methoxy-7-[methyl-(tetrahydro-pyran-4-yl)-amino]-benzothiazol-2-yl}-isonicotinamide a) (4-Methoxy-3-nitro-phenyl)-methyl-(tetrahydro-pyran-4-yl)-amine To a stirred solution of 7.50 g (32.0(mmol) 4-bromo-2-nitro-anisole in 200 ml dioxane were added 6.86 g (45.0 mmol) methyl-(tetrahydro-pyran-4-yl)-amine hydrochloride (1:1), 1.13 g (3.0 mmol) 2-(dicyclohexylphosphino) biphenyl, 14.75 g (45.0 mmol) cesium carbonate, and 360 mg (2.0 mmol) palladium (II) acetate. The mixture was heated at reflux for 72 h and then poured onto water and extracted three times with ethyl acetate. The combined organic phases were dried over sodium sulfate and concentrated in vacuo. Flash chromatography (1/2 hexane/ethyl acetate) afforded 1.59 g (18.5%) (4-methoxy-3-nitro-phenyl)-methyl-(tetrahydro-pyran-4-yl)-amine as a red solid. ES-MS m/e (%): 267 (M+H$^+$, 100).

b) 4-Methoxy-N1-methyl-N1-(tetrahydro-pyran-4-yl)-benzene-1,3-diamine

To a stirred solution of 0.73 g (2.74 mmol) (4-methoxy-3-nitro-phenyl)-methyl-(tetrahydro-pyran-4-yl)-amine in 50 ml methanol was added 15 mg 10% palladium on charcoal and the mixture was then stirred for 18 hours at room temperature under an atmosphere of hydrogen. The mixture was then filtered and the filtrate concentrated in vacuo to afford 0.3520 g (54%) 4-methoxy-N1-methyl-N1-(tetrahydro-pyran-4-ylmethyl)-benzene-1,3-diamine as an off-white solid. Mp.: 97–99° C.

c) 1-Benzoyl-3-{2-methoxy-5-[methyl-(tetrahydro-pyran-4-yl)-amino]-phenyl}-thiourea To a stirred solution of 0.330 g (1.4 mmol) 4-methoxy-N1-methyl-N1-(tetrahydro-pyran-4-ylmethyl)-benzene-1,3-diamine in 5 ml acetone was added dropwise 0.2 ml (1.50 mmol) benzoyl isothiocyanate and stirring continued for 16 hrs at room temperature. The mixture was then concentrated in vacuo and the residue subjected to column chromatography (1/1 hexane/ethyl acetate) to afford 0.31 g (56%) 1-benzoyl-3-{2-methoxy-5-[methyl-(tetrahydro-pyran-4-yl)-amino]-phenyl}-thiourea as a yellow solid. ES-MS m/e (%): 422 (M+Na$^+$, 13), 400 (M+H$^+$, 100).

d) {2-Methoxy-5-[methyl-(tetrahydro-pyran-4-yl)-amino]-phenyl}-thiourea

To a stirred suspension of 1.7 g (4.2 mmol) 1-benzoyl-3-{2-methoxy-5-[methyl-(tetrahydro-pyran-4-yl)-amino]-phenyl}-thiourea in 13 ml methanol was added dropwise 0.78 ml (6.35 mmol) 5.4 M sodium methylate solution and stirring continued for 18 hrs at room temperature. The mixture was then concentrated in vacuo and the residue subjected to column chromatography (1/1 hexane/ethyl acetate) to afford 0.6 g (51%) {2-methoxy-5-[methyl-(tetrahydro-pyran-4-yl)-amino]-phenyl}-thiourea as a yellow solid. ES-MS m/e (%): 296 (M+H$_+$, 100).

e) 4-Methoxy-N7-methyl-N7-(tetrahydro-pyran-4-yl)-benzothiazole-2,7-diamine 0.28 g (0.95 mmol) {2-methoxy-5-[methyl-(tetrahydro-pyran-4-yl)-amino]-phenyl}-thiourea were dissolved in 15 ml chloroform and 0.05 ml (1.0 mmol) Br$_2$ were added slowly at room temperature. After 24 hrs of reflux the mixture was concentrated in vacuo and the residue suspended in water. Sodium bicarbonate solution was added until the pH was 10, and the crystals were collected by filtration. These were subjected to column chromatography (ethyl acetate) to afford 0.41 g (41 (‰) of 4-methoxy-N7-methyl-N7-(tetrahydro-pyran-4-yl)-benzothiazole-2,7-diamine as an off-white solid. ES-MS m/e (%): 294 (M+H$^+$, 100).

f) 2-Bromo-N-{4-methoxy-7-[methyl-(tetrahydro-pyran-4-yl)-amino]-benzothiazol-2-yl}-isonicotinamide To a stirred solution of 103 mg (0.51 mmol) 2-bromo-isonicotinic acid in 3 ml THF were added 204 mg (0.53 mmol) HATU and 0.11 ml (1.02 mmol) N-methylmorpholine and stirring continued at 30° C. for 7 h. 75 mg (0.26 mmol) 4-methoxy-N7-methyl-N7-(tetrahydro-pyran-4-yl)-benzothiazole-2,7-diamine was then added and stirring continued at 40° C. for 16 h. The reaction mixture was then diluted with ethyl acetate and washed sequentially with saturated sodium bicarbonate solution and brine. The organic phase was dried over sodium sulfate and concentrated in vacuo. Flash chromatography (methanol/dichloromethane) followed by trituration in ether/pentane afforded 77 mg (63%) 2-bromo-N-{4-methoxy-7-[methyl-(tetrahydro-pyran-4-yl)-amino]-benzothiazol-2-yl}-isonicotinamide as a white crystalline solid. ES-MS m/e (%): 479 (M{$^{81}$Br}+H$^+$, 100), 477 (M{$^{79}$Br}+H$^+$, 95).

In an analogous manner there was obtained:

EXAMPLE 37

4-Fluoro-N-{4-methoxy-7-[methyl-(tetrahydro-pyran-4-yl)-amino]-benzothiazol-2-yl}-benzamide From 4-methoxy-N7-methyl-N7-(tetrahydro-pyran-4-ylmethyl)-benzothiazole-2,7-diamine with 4-fluorobenzoic acid, HATU and N-ethyldiisopropylamine in THF. ES-MS m/e (%): 416 (M+H⁺, 100).

Analogously to Example 6 there were obtained:

EXAMPLE 38

N-{4-Methoxy-4-[methyl-(tetrahydro-pyran-4-yl)-amino]-benzothiazol-2-yl}-2-morpholin-4-yl-isonicotinamide From 2-bromo-N-{4-methoxy-7-L methyl-(tetrahydro-pyran-4-yl)-amino]-benzothiazol-2-yl}-isonicotinamide with morpholine and cesium carbonate. ES-MS m/e (%): 484 (M+H⁺, 100).

We claim:

1. A compound of the formula I

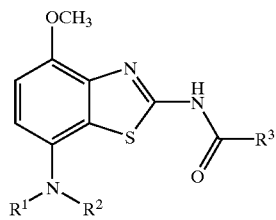

wherein
R¹ and R² are independently selected from the group consisting of hydrogen, lower alkyl, $C_{3-6}$-cycloalkyl, tetrahydropyran-2,3 or ⁴-yl, piperidin-4-yl, piperidin-4-yl substituted by lower alkyl, —(CH₂)ₙ—O-lower alkyl, —(CH₂)ₙ—NR'R", —C(O)-lower alkyl, —(CH₂)ₙ—C(O)-lower alkyl, —(CH₂)ₙ—C(O)—$C_{3-6}$-cycloalkyl, —(CH₂)ₙ—C(O)—NR'R", —(CH₂)ₙ-phenyl, —(CH₂)ₙ-phenyl substituted by lower alkyl, lower alkoxy or NR'R", —(CH₂)ₙ-pyridinyl, —(CH₂)ₙ-pyridinyl substituted by lower alkyl, lower alkoxy or NR'R", —(CH₂)ₙ-morpholinyl, —(CH₂)ₙ-tetrahydropyran-2,3 or 4-yl, —(CH₂)ₙ-piperidin-1 or 4-yl, —(CH₂)ₙ-piperidin-1 or 4-yl substituted by lower alkyl, —C(O)—$C_{5,6}$-cycloalkyl, —C(O)-tetrahydropyran-2,3 or 4-yl, —C(O)-morpholinyl, —C(O)-piperidin-1-yl and —C(O)-pyrrolidin-1-yl, or R¹ and R² form together with the N atom to which they are attached the ring 2-oxa-5-aza-bicyclo[2.2.1]hept-5-yl, an azetidinyl ring, or an azetidinyl ring substituted by lower alkyl or lower alkoxy;

R³ is lower alkoxy, phenyl, phenyl substituted by halogen, —(CH₂)ₙ-halogen, or —(CH₂)ₙ—N(R')—(CH₂)ₙ₊₁—O-lower alkyl, pyridinyl, pyridinyl substituted by lower alkyl, halogen or morpholinyl, morpholinyl, piperidin-1-yl disubstituted in the 4 position by lower alkyl and —(CH₂)ₙ—OH, or 2-aza-bicyclo[2.2.2] octane;

n is 1 or 2;

R' and R" are each independently selected from hydrogen or lower alkyl or together may form with the N atom an azetidinyl-, pyrrolidinyl- or piperidinyl group;

and pharmaceutically acceptable acid addition salts thereof.

2. The compound according to claim 1, wherein one of R¹ and R² is lower alkyl and the other is —(CH₂)ₙ—O-lower alkyl and R³ is phenyl, or phenyl substituted by halogen or (CH₂)ₙ-halogen.

3. The compound according to claim 2, wherein the compound is selected from the group consisting of:

N-{4-methoxy-7-[(2-methoxy-ethyl)-methyl-amino]-benzothiazol-2-yl}-benzamide, 4-fluoro-N-{4-methoxy-7-[(2-methoxy-ethyl)-methyl-amino]-benzothiazol-2-yl}-benzamide and 4-chloromethyl-N-{4-methoxy-7-[(2-methoxy-ethyl)-methyl-amino]-benzothiazol-2-yl}-benzamide.

4. The compound according to claim 1, wherein one of R₁ and R² is lower alkyl and the other is —(CH₂)ₙ—O-lower alkyl, or R₁ and R² are together with the N atom the group 2-oxa-5-aza-bicyclo[2.2.1]hept-5-yl and R³ is pyridinyl, substituted by morpholine.

5. The compound according to claim 4, wherein the compound is selected from the group consisting of:

N-{4-methoxy-7-[(2-methoxy-ethyl)-methyl-amino]-benzothiazol-2-yl}-2-morpholin-4-yl-isonicotinamide and N-[4-methoxy-7-{(1S,4S)-(2-oxa-5-aza-bicyclo[2.2.1]hept-5-yl)}-benzothiazol-2-yl]-2-methyl-isonicotinamide.

6. The compound according to claim 1, wherein one of R¹ and R² is —C(O)-lower alkyl and the other is lower alkyl, —(CH₂)ₙ—O-lower alkyl, benzyl, or benzyl substituted by lower alkyl, and R³ is phenyl or pyridinyl, which rings are optionally substituted by halogen or lower alkyl.

7. The compound according to claim 6, wherein the compound is selected from the group consisting of:

N-{7-[acetyl-(4-methyl-benzyl)-amino]-4-methoxy-benzothiazol-2-yl}-benzamide,

N-[7-(acetyl-methyl-amino)-4-methoxy-benzothiazol-2-yl]-4-fluoro-benzamide,

N-[7-(acetyl-ethyl-amino)-4-methoxy-benzothiazol-2-yl]-4-fluoro-benzamide,

N-[7-(acetyl-benzyl-amino)-4-methoxy-benzothiazol-2-yl]-4-fluoro-benzamide,

N-[7-(acetyl-benzyl-amino)-4-methoxy-benzothiazol-2-yl]-2-bromo-isonicotinamide and N-{7-[acetyl-(2-methoxy-ethyl)-amino]-4-methoxy-benzothiazol-2-yl}-4-fluoro-benzamide.

8. The compound according to claim 1, wherein one of R¹ and R² is lower alkyl and the other is lower alkyl, benzyl, or benzyl substituted by lower alkoxy, and R₃ is substituted or unsubstituted phenyl or substituted or unsubstituted pyridinyl, wherein when R³ is substituted, the substituent being morpholinyl, halogen or lower alkyl.

9. The compound according to claim 8, wherein the compound is selected from the group consisting of:

N-(7-dimethylamino-4-methoxy-benzothiazol-2-yl)-4-fluoro-benzamide,

N-[7-(benzyl-methyl-amino)-4-methoxy-benzothiazol-2-yl]-4-fluoro-benzamide,

N-[7-(benzyl-methyl-amino)-4-methoxy-benzothiazol-2-yl]-2-methyl-isonicotinamide, 4-fluoro-N-{4-methoxy-7-[(4-methoxy-benzyl)-methyl-amino]-benzothiazol-2-yl}-benzamide, N-{4-methoxy-7-[(4-methoxy-benzyl)-methyl-amino]-benzothiazol-2-yl}-2-methyl-isonicotinamide, N-[7-(benzyl-methyl-amino)-4-methoxy-benzothiazol-2-yl]-2-bromo-isonicotinamide and N-[7-(benzyl-methyl-amino)-4-methoxy-benzothiazol-2-yl]-2-morpholin-4-yl-isonicotinamide.

10. The compound according to claim 1, wherein one of R¹ and R² is lower alkyl and the other is —CH₂—C(O)—N(CH₃)₂ or tetrahydropyran, and R³ is substituted or unsubstituted phenyl or substituted or unsubstituted pyridinyl, wherein when R³ is substituted the substituent being morpholinyl, halogen or lower alkyl.

11. The compound according to claim 10, wherein the compound is selected from the group consisting of:

N-[7-(dimethylcarbamoylmethyl-methyl-amino)-4-methoxy-benzothiazol-2-yl]-4-fluoro-benzamide, N-[7-(dimethylcarbamoylmethyl-ethyl-amino)-4-methoxy-benzothiazol-2-yl]-4-fluoro-benzamide, 4-fluoro-N-{4-methoxy-7-[methyl-(tetrahydro-pyran-4-yl)-amino]-benzothiazol-2-yl}-benzamide and N-{4-methoxy-7-[methyl-(tetrahydro-pyran-4-yl)-amino]-benzothiazol-2-yl}-2-morpholin-4-yl-isonicotinamide.

12. A process for preparing a compound of formula I as defined in claim 1, which process comprises:

reacting a compound of formula

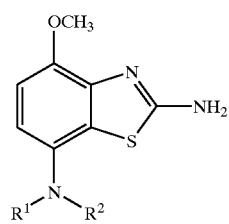

(7)

with a compound of formula

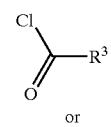

(8)

or

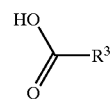

(9)

to yield a compound of formula

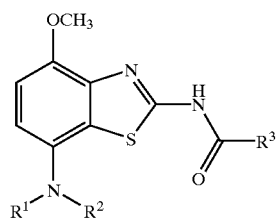

I wherein $R_1$, $R^2$ and $R^3$ are as defined in claim 1, and optionally converting the compounds obtained into pharmaceutically acceptable acid addition salts.

13. A method of treating a disease mediated by the adenosine receptor comprising administering to a patient in need of such treatment, an effective amount of a compound of the formula I

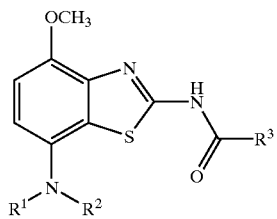

I wherein $R^1$ and $R^2$ are independently selected from the group consisting of hydrogen, lower alkyl, $C_{3-6}$-cycloalkyl, tetrahydropyran-2,3 or 4-yl, piperidin-4-yl, piperidin-4-yl substituted by lower alkyl, —$(CH_2)_n$—O-lower alkyl, —$(CH_2)_n$—NR'R", —C(O)-lower alkyl, —$(CH_2)_n$—C(O)-lower alkyl, —$(CH_2)_n$—C(O)—$C_{3-6}$-cycloalkyl, —$(CH_2)_n$—C(O)—NR'R", —$(CH_2)_n$-phenyl, —$(CH_2)_n$-phenyl substituted by lower alkyl, lower alkoxy or NR'R", —$(CH_2)_n$-pyridinyl, —$(CH_2)_n$-pyridinyl substituted by lower alkyl, lower alkoxy or NR'R", —$(CH_2)_n$-morpholinyl, —$(CH_2)_n$-tetrahydropyran-2,3 or 4-yl, —$(CH_2)_n$-piperidin-1 or 4-yl, —$(CH_2)_n$-piperidin-1 or 4-yl substituted by lower alkyl, —C(O)—$C_{5,6}$-cycloalkyl, —C(O)-tetrahydropyran-2,3 or 4-yl, —C(O)-morpholinyl, —C(O)-piperidin-1-yl and —C(O)-pyrrolidin-1-yl, or $R_1$ and $R^2$ form together with the N atom to which they are attached the ring 2-oxa-5-aza-bicyclo[2.2.1]hept-5-yl, an azetidinyl ring, or an azetidinyl ring substituted by lower alkyl or lower alkoxy;

$R^3$ is lower alkoxy, phenyl, phenyl substituted by halogen, —$(CH_2)_n$-halogen, or —$(CH_2)_n$—N(R')—$(CH_2)_n$—O-lower alkyl, pyridinyl, pyridinyl substituted by lower alkyl, halogen or morpholinyl, morpholinyl, piperidin-1-yl disubstituted in the 4 position by lower alkyl and —$(CH_2)_n$—OH, or 2-aza-bicyclo[2.2.2]octane;

n is 1 or 2;

R' and R" are each independently selected from hydrogen or lower alkyl or together may form with the N atom an azetidinyl-, pyrrolidinyl- or piperidinyl group;

and pharmaceutically acceptable acid addition salts thereof.

14. The method according to claim 13, wherein said disease is selected from at least one of Alzheimer's disease, Parkinson's disease, Huntington's disease, neuroprotection, schizophrenia, anxiety, pain, respiration deficits, depression, drug addiction, asthma, allergic responses, hypoxia, ischaemia, seizure, and attention deficit hyperactivity disorder.

15. The method according to claim 13, wherein said adenosine receptor is the $A_{2A}$ receptor.

16. The method according to claim 15, wherein said disease is selected from the group consisting of Alzheimer's disease, depression, drug addiction, neuroprotection, Parkinson's disease, and attention deficit hyperactivity disorder.

17. A pharmaceutical composition comprising a pharmaceutically effective amount of a compound of the formula I

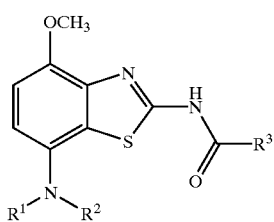

wherein

R$^1$ and R$^2$ are independently selected from the group consisting of hydrogen, lower alkyl, C$_{3-6}$-cycloalkyl, tetrahydropyran-2,3 or 4-yl, piperidin-4-yl, piperidin-4-yl substituted by lower alkyl, —(CH$_2$)$_n$—O-lower alkyl, —(CH$_2$)$_n$—NR'R", —C(O)-lower alkyl, —(CH$_2$)$_n$—C(O)-lower alkyl, —(CH$_2$)$_n$—C(O)—C$_{3-6}$-cycloalkyl, —(CH$_2$)$_n$—C(O)—NR'R", —(CH$_2$)$_n$-phenyl, —(CH$_2$)$_n$-phenyl substituted by lower alkyl, lower alkoxy or NR'R"—(CH$_2$)$_n$-pyridinyl, —(CH$_2$)$_n$-pyridinyl substituted by lower alkyl, lower alkoxy or NR'R", —(CH$_2$)$_n$-morpholinyl, —(CH$_2$)$_n$-tetrahydropyran-2,3 or 4-yl, —(CH$_2$)$_n$-piperidin-1 or 4-yl, —(CH$_2$),-piperidin-1 or 4-yl substituted by lower alkyl, —C(O)—C$_{5,6}$-cycloalkyl, —C(O)-tetrahydropyran-2,3 or 4-yl, —C(O)-morpholinyl, —C(O)-piperidin-1-yl and —C(O)-pyrrolidin-1-yl, or R$^1$ and R$^2$ form together with the N atom to which they are attached the ring 2-oxa-5-aza-bicyclo[2.2.1]hept-5-yl, an azetidinyl ring, or an azetidinyl ring substituted by lower alkyl or lower alkoxy;

R$^3$ is lower alkoxy, phenyl, phenyl substituted by halogen, —(CH$_2$),-halogen, or —(CH$_2$)$_n$—N(R')—(CH$_2$)$_{n+1}$—O-lower alkyl, pyridinyl, pyridinyl substituted by lower alkyl, halogen or morpholinyl, morpholinyl, piperidin-1-yl disubstituted in the 4 position by lower alkyl and —(CH$_2$)$_n$—OH, or 2-aza-bicyclo[2.2.2]octane;

n is 1 or 2;

R' and R" are each independently selected from hydrogen or lower alkyl or together may form with the N atom an azetidinyl-, pyrrolidinyl- or piperidinyl group;

and pharmaceutically acceptable acid addition salts thereof; and a pharmaceutically acceptable carrier.

* * * * *

UNITED STATES PATENT AND TRADEMARK OFFICE
CERTIFICATE OF CORRECTION

PATENT NO. : 6,713,499 B2
DATED : March 30, 2004
INVENTOR(S) : Alexander Flohr et al.

It is certified that error appears in the above-identified patent and that said Letters Patent is hereby corrected as shown below:

Title page,
Item [73], Assignee, delete "Hoffman-La Roche Inc., Nutley, NJ (US)" and insert -- Hoffmann-La Roche Inc., Nutley, NJ (US) --.

Column 29,
Line 28, delete "tetrahydropyran-2,3 or $^4$-yl, piperidin-4-yl, piperidin-" and insert -- tetrahydropyran-2,3 or 4-yl, piperidin-4-yl, piperidin- --.
Line 59, delete "." and insert -- provided that, when one of $R^1$ and $R^2$ is C(O)-lower alkyl, the other is not hydrogen. --.

Column 30,
Lines 43-44 and 66-67, delete ", wherein when $R^3$ is substitute the substituent being morpholinyl, halogen or lower alkyl".

Column 32,
Line 38, delete "-$(CH_2)_n$-halogen, or  -$(CH_2)_n$-N(R')-$(CH_2)_n$-O-" and insert -- -$(CH_2)_n$-halogen, or -$(CH_2)_n$-N(R')-$(CH_2)_{n+1}$-O- --.
Line 51, delete "." and insert -- provided that when one of $R^1$ and $R^2$ is –C(O)-lower alkyl, the other is not hydrogen. --.

Column 34,
Line 22, delete ";" and insert -- provided that, one of $R^1$ and $R^2$ is –C(O)-lower alkyl, the other is not hydrogen; --.

Signed and Sealed this

Twenty-fifth Day of January, 2005

JON W. DUDAS
*Director of the United States Patent and Trademark Office*